United States Patent [19]

Fendrich et al.

[11] Patent Number: 5,093,247
[45] Date of Patent: Mar. 3, 1992

[54] PHENANTHRIDINE DERIVATIVES, PROCESS FOR THE PREPARATION THEREOF, AND COMPOSITIONS CONTAINING THEM

[75] Inventors: Gabriele Fendrich, Basel; Willy Zimmermann, Buus; Johannes Gruner, Flüh; John A. L. Auden, Reinach, all of Switzerland

[73] Assignee: Ciba-Geigy Corporation, Ardsley, N.Y.

[21] Appl. No.: 477,087

[22] Filed: Feb. 8, 1990

Related U.S. Application Data

[62] Division of Ser. No. 230,941, Aug. 11, 1988, Pat. No. 4,939,158.

[30] Foreign Application Priority Data

Aug. 20, 1987 [CH] Switzerland ............... 3196/87

[51] Int. Cl.$^5$ ............... C12P 17/04; C07D 221/12
[52] U.S. Cl. ............... 435/119; 435/122; 435/886; 536/17.4; 546/61
[58] Field of Search ............... 546/61; 435/122, 886, 435/119; 536/17.4

[56] References Cited

U.S. PATENT DOCUMENTS 3,131,126  4/1964  Gaeumann et al. ............... 435/886
4,600,691  7/1986  Chaiet et al. ............... 435/886

FOREIGN PATENT DOCUMENTS 128670  12/1984  European Pat. Off. .
298385  1/1989  European Pat. Off. .

OTHER PUBLICATIONS

Klemm et al., J. Heterocyclic Chem., vol. 2, No. 1, pp. 15-20 (1965).
Khokhlox et al., Chem. Abstract, vol. 103, No. 17, 142223u.
Arlandini et al., Il Farmaco-Ed. Sc., vol. 32, No. 5, pp. 315-323 (1977).
Israel et al., Chemical Abst., vol. 105, No. 24506g (1986).
J. Chem. Soc. Perk. Trans., vol. 1, pp. 997-1000 (1976).
Kunstmann et al., J. Org. Chem., vol. 31, No. 9, pp. 2920-2925 (1966).

Primary Examiner—Robert T. Bond
Assistant Examiner—E. C. Ward
Attorney, Agent, or Firm—JoAnn Villamizar

[57] ABSTRACT

The invention relates to 1,8-dihydroxy-3-methyl-benz[b]phenanthridine-7,12-dione and its derivatives of formula I

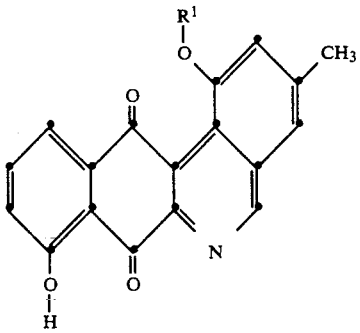

wherein $R^1$ is hydrogen or the radical of formula II

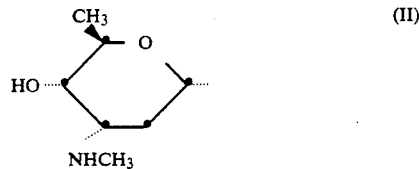

and salts of the compound, wherein $R^1$ is the radical of formula II. These compounds can be obtained by means of a novel microbiological process and used for the therapeutic treatment of tumors.

4 Claims, No Drawings

PHENANTHRIDINE DERIVATIVES, PROCESS FOR THE PREPARATION THEREOF, AND COMPOSITIONS CONTAINING THEM

This is a divisional of application Ser. No. 230,941 filed on Aug. 11, 1988, now U.S. Pat. No. 4,939,158.

The present invention relates to specific benzo[b]phenanthridine derivatives, namely 1,8-dihydroxy-3-methylbenzo[b]phenanthridine-7,12-dione and specific derivatives thereof, to a process for the preparation of these compounds, to microorganisms for carrying out the preparatory process, to pharmaceutical compositions containing such a phenanthridine derivative, and to the use of these compounds as antineoplastic agents.

Specifically, the invention relates to 1,8-dihydroxy-3-methylbenzo[b]phenanthridine-7,12-dione and its derivative of formula I

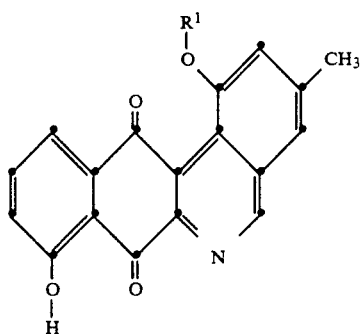

wherein $R^1$ is hydrogen or the radical of formula II

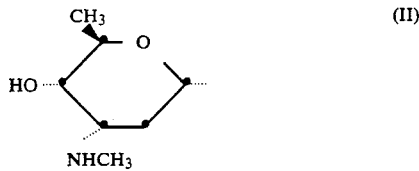

and to salts of said compound, wherein $R^1$ is a radical of formula II, to a process for the preparation of these compounds, to microorganisms for carrying out the preparatory process, to pharmaceutical compositions containing such a phenanthridine derivative, and to the use of said compounds as antineoplastic agents.

According to NMR spectroscopy, the radical of formula II has the relative configuration indicated above and also expressed by the following equivalent formula IIa:

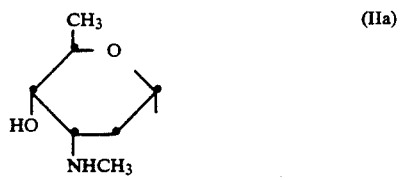

The radical of formula II is in optically active form. Its absolute configuration is still unknown, but can be unequivocally defined by the preparatory process.

The present invention relates in particular to the compound of formula I, wherein $R^1$ is the optically active radical of formula II in the absolute configuration obtainable by culturing the strain Streptomyces viridochromogenes DSM 3972. This compound is designated hereinafter as phenanthroviridine. According to IUPAC nomenclature, phenanthroviridine is named as 1-(2,3,6-trideoxy-3-methylamino-α-ribo-hexopyranosyloxy)-8-hydroxy-3-methylbenzo[b]phenanthridine-7,12-dione. In this name, the prefix "ribo", like the prefix "erythro" or "threo", indicates only the relative configuration at the centres of asymmetry in positions 3, 4 and 5 of the 2,3,6-trideoxy-3-methylaminohexopyranosyl radical. The configurational prefix "α" does not refer to "ribo", but defines the relative configuration in 1-position of the hexopyranosyl radical. The absolute configuration, i.e. the assignment to the D- or L-series, remains open. Alternatively, phenanthroviridine can also be named as 1-(2,3,6-trideoxy-3-methylamino-α-allopyranosyloxy)-8-hydroxy-3-methylbenzo[b]phenanthridine-7,12-dione.

Salts of a compound of formula I are preferably pharmaceutically acceptable non-toxic salts, i.e. acid addition salts with inorganic acids such as hydrochloric acid, sulfuric acid or phosphoric acid, or with suitable organic carboxylic or sulfonic acids, for example trifluroacetic acid, and with amino acids such as argenine and lysine.

For isolation or purification it is also possible to use pharmaceutically unacceptable salts. For therapeutic use, however, only the pharmaceutically acceptable non-toxic salts are eligible and for this reason preferred.

The compounds of formula I and the pharmaceutically acceptable salts thereof have valuable pharmacological properties, in particular tumoricidal properties, when administered to warm-blooded animals including humans, as can be demonstrated e.g. by treating experimental tumors, for example human lung carcinoma MBA 9812. Thus compounds of formula I, when administered in a daily dose ranging from 5 to 20 mg/kg i.p., reduces the weight (25 mg) of lung carcinoma MBA 8912, which has been implanted in black nude female C-57 mice having a body weight of 18-22 g, to ca. 10% compared with untreated animals after 14-15 daily doses. Administration of a twice daily dose of 5 mg/kg i.p. of the compound of formula I, wherein $R^1$ is hydrogen (aglycon), over 15 days effects a reduction in tumor weight of around 96% to only just 4%.

The process for the preparation of compounds of formula I or a salt of the compound, wherein $R^1$ is the radical of formula II, comprises culturing the strain Streptomyces viridochromogenes (Krainsky) Waksman et Henrici (without formation of melanin) DSM 3972, or a culture derivable therefrom, in a suitable nutrient medium, isolating the compound of formula I, wherein $R^1$ is the radical of formula II, from the culture broth and, if desired, converting the resultant compound into a salt and, if desired, into the compound of formula I, wherein $R^1$ is hydrogen, by treatment with an acidic means.

The above described process will now be explained in more detail.

The compounds of formula I are obtained by means of a novel microbiological process, namely by fermentation with the novel strain Streptomyces viridochromogenes (Krainsky) Waksman et Henrici (without formation of melanin) which was deposited in accordance with the provisions of the Budapest Treaty on the International Recognition of the Deposit of Microorganisms for the Purposes of Patent Procedure on Feb. 2, 1987, with the Deutsche Sammlung für Mikroorganismen (German Collection for Microorganisms), Grisebachstrasse 8, D-3400 Göttingen, Federal Republic of Germany, under the accession number DSM 3972.

The strain was isolated in 1983 from a soil sample taken from a tropical virgin forest in the region of Ribeirao Preto, Sao Paulo Province, Brazil. Determination of the strain was made in accordance with R. Hütter, "Systematik der Streptomyceten", Verlag Karger, Basel, 1967, p. 96 et seq. (L,L)-Diaminopimelic acid can be detected in cell hydrolysates. Neither on peptone/agar nor on tyrosine/agar does the strain DSM 3972 form a melanoid dye. This feature is in contrast to the hitherto known representatives of Streptomyces viridochromogenes. The agars used for testing the melanin formation have the following composition:

|  | g/liter |
|---|---|
| Peptone-iron-agar (pH 7.4) | |
| yeast extract | 1 |
| bactopeptone | 15 |
| iron-ammonium-citrate | 0.5 |
| $K_2HPO_4$ | 1 |
| $Na_2S_2O_3$ | 0.08 |
| bacto agar | 15 |
| Synthetic medium (pH 7.4) | |
| tyrosine | 1 |
| glycerol | 15 |
| L-arginine-HCl | 5 |
| methionine | 0.3 |
| $K_2HPO_4$ | 0.5 |
| $MgSO_4 \times 7 H_2O$ | 0.02 |
| $CuSO_4 \times 5 H_2O$ | 0.01 |
| $CaCl_2 \times 2 H_2O$ | 0.01 |
| $FeSO_4 \times 7 H_2O$ | 0.01 |
| $ZnSO_4 \times 7 H_2O$ | 0.01 |
| $MnSO_4 \times 7 H_2O$ | 0.04 |
| bacto agar | 15 |

The strain DSM 3972 utilises the following sugars and alcohols: arabinose, xylose, rhamnose, raffinose, mannitol, inisotol, fructose, saccharose, glucose, lactose, cellobiose and adonite. No growth is observed on insulin. The test for carbohydrate utilisation is carried out in the following medium:

| Basic medium (ATCC 623; pH 7.0) | | |
|---|---|---|
| L-glutamic acid | 20 | g/liter |
| $(NH_4)_2SO_4$ | 4 | " |
| $MgSO_4 \times 7 H_2O$ | 0.2 | " |
| $K_2HPO_4$ | 1.88 | " |
| $KH_2PO_4$ | 0.57 | " |
| salt solution* | 10 | ml/litre |
| carbohydrate to be tested | 10 | g/liter |

*The above salt solution has the following composition:

| Salt solution | g/liter |
|---|---|
| $FeCl_3 \times 6 H_2O$ | 0.6 |
| $MnCl_2 \times 4 H_2O$ | 0.6 |
| $CuSO_4 \times 5 H_2O$ | 0.6 |
| $CaCl_2 \times 2 H_2O$ | 0.6 |
| $ZnCl_2$ | 0.6 |
| NaCl | 0.6 |

The strain DSM 3972 conforms in some features to Streptomyces albocyaneus, but in contradistinction thereto does not form an endopigment.

The following overview lists further data for characterising the strain DSM 3972:

| Morphology | |
|---|---|
| substrate mycelium: | yellowish brown |
| air mycelium: | beige-brown, later greenish blue |
| spore colour: | greenish blue |
| spore chains: | short, narrow spirals |
| spore form: | spherical-ellipsoid |
| spore surface: | spiny |
| Culture medium | |
| Yeast agar (pH 7.0) | g/liter |
| yeast extract | 4 |
| malt extract | 5 |
| glucose | 4 |
| agar | 20 |

A derivable culture in the above sense will be understood as meaning any culture which in addition has the features of the deposited culture essential for carrying out the process of the invention, i.e. mainly a derived culture, especially a culture whose microorganisms contain the same structural genes as those of the strain DSM 3972 essential for the formation of the compound of formula I. A derivable culture will also be understood as meaning any culture whose microorganisms contain an equivalent of the structural genes of strain DSM 3972 essential for the formation of the compound of formula I, which equivalent is possible owing to the degeneration of the genetic code. In particular, a derivable culture will be understood as meaning any culture which contains microorganisms of the genus Streptomyces, preferably of the species Streptomyces viridochromogenes, which are capable of producing the compound of formula I. The term "derivable culture of the the strain DSM 3972" also includes all mutants of said strain which are capable of producing the compound of formula I.

The nutrient medium used is preferably an aqueous solution or suspension which contains at least one carbon source and at least one nitrogen source and preferably also mineral substances. Examples of carbon sources are: glycerol, assimilable carbohydrates such as cyclitols, for example mannitol, polysaccharides, for example starch, disaccharides, for example lactose and saccharose, and monosaccharides, especially glucose and fructose, as well as corresponding industrial raw materials which contain carbohydrates, for example molasses obtained from sugar beet or sugar cane. Typical nitrogen sources are: amino acids, in particular the α-amino acids occurring in nature, peptides as well as proteins and their degradation products such as peptones and tryptones, and also ammonium salts and nitrates, as well as appropriate nitrogen-containing raw materials such as meat extracts, casein hydrolysate and yeast autosylate and yeast extract. Mixed carbon and nitrogen sources are also suitable, such as different plant seeds that are used in the form of aqueous extracts, flour or mashes, for example of beans such as soybeans, cereal grains, for example wheat, and, in particular, maize (corn-steep liquor); and also cotton seeds and malt extract. In addition to ammonium salts, in particular ammonium chloride, ammonium sulfate or ammonium nitrate and further nitrates, the nutrient medium can also contain inorganic salts such as chlorides, carbonates, sulfates and, preferably, phosphates of alkali metals and alkaline earth metals, in particular of sodium, potassium, magnesium and calcium, as well as of trace elements such as iron, zinc and manganese.

The nutrient medium is sterilised and inoculated with a culture of the production strain while maintaining the usual conditions.

Culturing is effected under aerobic conditions, for example in dormant surface culture or, preferably, beneath the surface while shaking or stirring with air or oxygen in shaking bottles or fermenters. The temperature is suitably in the range from ca. 15° to 40° C., preferably from ca. 22° to 32° C. The most preferred temperature is ca. 28° C. The fermentation time is preferably from 2 to 12 days, for example 7 or 8 days. Culturing is preferably carried out in several steps, i.e. one or more precultures are first prepared in liquid nutrient medium and are then used to inoculate the actual production medium, for example in the ratio of 1:20.

Isolation is effected by physico-chemical methods by means of per se known separating methods, especially by centrifugation, filtration, solvent extraction, precipitation, crystallisation and chromatography, preferably adsorption and distribution chromatography.

Preferably the culture broth is first acidified, for example with 50% sulfuric acid, to ca. pH 2 and extracted with a suitable solvent, for example ethyl acetate, to remove impurities. The extract is discarded. The raffinate and mycelium are adjusted with a suitable alkali, for example 5N NaOH, to ca. pH 10 and extracted with a suitable solvent, for example ethyl acetate. The concentrated extract is purified by partitioning it e.g. between a suitable alcohol such as methanol and a suitable non-polar organic solvent, for example a hydrocarbon such as heptane. The alcoholic phase is concentrated by evaporation and the residue is chromatographed on silica gel. The main fraction is further purified in slightly acidic medium by reverse phase chromatography. The fractions containing the desired product are lyophilised. The lyophilisate is chromatographed on a modified dextran gel, e.g. Sephadex ®, and subsequently crystallised.

The conversion of the compound of formula I, wherein $R^1$ is a radical of formula II, into the aglycon is effected with an acidic means such as a mineral acid or an acid ion exchanger, preferably by heating the trifluoroacetate in dilute hydrochloric acid, for example 0.1N HCl, to 50°-120° C., for example 90° C. The aglycon precipitates and the precipitate is isolated by filtration, taken up in a suitable organic solvent, for example chloroform, and purified by extraction with water and crystallisation of the dried organic phase.

The invention relates in particular to a process for the preparation of phenanthroviridine, which comprises culturing, under aerobic conditions, the strain Streptomyces viridochromogenes DSM 3972 or a microorganism which contains the same structural genes as those of the said strain essential for the formation of phenanthroviridine, in an aqueous nutrient medium containing a carbon source and a nitrogen source as well as inorganic salts, and isolating the phenthroviridine so obtained.

The invention relates first and foremost to an embodiment of the above process, which comprises culturing a microorganism of the species Streptomyces viridochromogenes which forms phenanthroviridine.

A preferred embodiment of the above process comprises culturing the strain Streptomyces viridochromogene DSM 3972 or a mutant thereof which forms phenanthrovidiridine.

A particularly preferred embodiment of the above process comprises culturing the strain Streptomyces viridochromogenes DMS 3972.

It is preferred to carry out the fermentation under the conditions described in the Examples.

Microorganisms which contain the same structural genes essential for the formation of phenanthroviridine as the strain DSM 3972 can be artificially produced, for example by gene manipulation, by isolating the corresponding structural genes from the strain DSM 3972 and inserting them at an appropriate site into the genetic material of another suitable microorganism. Suitable microorganisms are those into which the structural genes in question can not only be inserted, but in which these structural genes can also be expressed and in which the phenanthroviridine is not degraded again and also, preferably, precipitated in the fermentation broth. Such suitable microorganisms are in particular other strains of the genus Streptomyces, most particularly those of the species Streptomyces viridochromogenes, provided they do not already possess the above mentioned structural genes.

After establishing the nucleotide sequence of the above mentioned structural genes, these can also be prepared synthetically. Because of the degeneration of the genetic code, the possibility exists of exchanging specific nucleotide sequences of three successive nucleotides, known as codons, for other codons which code for the same amino acid.

Mutants forming phenanthroviridine can be produced, for example, by treatment with ultraviolet or X-rays or with chemical mutagenes, for example N-methyl-N'-nitro-N-nitrosoguanidine, and isolated in a manner known per se by selection according to their specific properties.

The invention also relates to a process for the preparation of a fermentation product that contains a detectable amount of phenanthroviridine, which process comprises culturing the strain Streptomyces viridochromogenes DSM 3972, or a culture derivable from said strain, in a nutrient medium, and discontinuing the process for isolating or purifying phenanthroviridine at the appropriate stage.

The invention also relates to the use of a compound of formula I for the medicinal treatment of diseases in warm-blooded animals including humans, in particular for treating tumors, for example lung tumors, by administering a therapeutically effective amount, for example a tumoricidal amount, of a compound of formula I. The dosage for administration to warm-blooded animals having a body weight of ca. 70 kg, for example to such a human, is 100 to 1000 mg per day. Administration is preferably made parenterally in the form of pharmaceutical compositions, for example intravenously or intraperitoneally.

The invention further relates to pharmaceutical compositions which contain a compound of formula I, especially an effective dose, for example a tumoricidal dose, of a compound of formula I, together with a pharmaceutical carrier, preferably a significant amount of a carrier.

The pharmacologically useful compounds of this invention can be used in the form of compositions for parenteral administration or of infusion solutions. Such solutions are preferably isotonic aqueous solutions or suspensions which, for example as lyophilised compositions that contain the active substance alone or together with a carrier, for example mannitol, can be prepared before use. The pharmaceutical compositions can be sterilised and/or contain adjuvants, for example preservatives, stabilisers, wetting agents and/or emulsifiers, solubilisers, salts for regulating osmotic pressure and/or buffers. The pharmaceutical compositions of this invention, which, if desired, may contain further pharmacologically active substances such as antibiotics, are prepared in a manner known per se, for example by conventional solubilising or lyophilising methods, and contain from ca. 0.1 to 90%, preferably from ca. 0.5 to 30%, for example 1 to 5%, of active substance or active substances.

The following Examples illustrate the invention without implying any restriction to what is described therein. The $R_f$ values are determined on thin-layer silica gel plates (ex Merck, Darmstadt, West Germany). The ratio of eluants to each other in the eluant mixtures employed is given in parts by volume (v/v). The concentration c of the substance in the solvent or mixture of solvents is expressed in % in the case of optical rotation (weight/volume).

The following abbreviations are used when indicating the nuclear resonance spectra:

b = broad
d = doublet
Hz = hertz
J = coupling constant
m = multiplet
q = quartet
s = singulet
t = triplet

EXAMPLE 1

21 liters of culture solution of pH 8.8 (from step 1.4) are adjusted to pH 2 with 50% sulfuric acid and stirred for 15 minutes in 50 liters of ethyl acetate. The acid ethyl acetate extract is discarded. The raffinate and mycelium are adjusted to pH 10 with 5N sodium hydroxide solution and stirred for 30 minutes in 110 liters of ethyl acetate. The basic ethyl acetate extract is concentrated by evaporation and the residual oil is partitioned between methanol and heptane. The heptane phase is discarded and the methanol phase is evaporated to dryness. The residue is chromatographed on 500 g of silica gel (elution with a mixture of methylene chloride/methanol/25% aqueous ammonia solution in the ratio 94:6:1). The dry residue of the main fraction (~1 g) is dissolved in acetonitrile/water/trifluoroacetic acid (50:50:1) and purified by reverse phase chromatography on Lichroprep ® ($C_1$–$C_4$alkyl modified silica gel, ex E. Merck, Darmstadt, West Germany). The fractions containing the desired product (phenanthroviridine) are lyophilised. The residue is chromatographed on Sephadex ®-LH 20 (modified dextran gel, ex Pharmacia, Sweden) with methanol as eluant. The crude product is crystallised from methanol/isopropanol, to give 1-(2,3,6-trideoxy-3-methylamino-α-ribohexopyranosyloxy)-8-hydroxy-3-methylbenzo[b]phenanthridine-7,12-dionetrifluoroacetate (phenanthroviridine trifluoroacetate) of m.p. 196°–197° C.; $[\alpha]_D^{20} = +62° \pm 1.9°$ (c=0.518 in methanol)

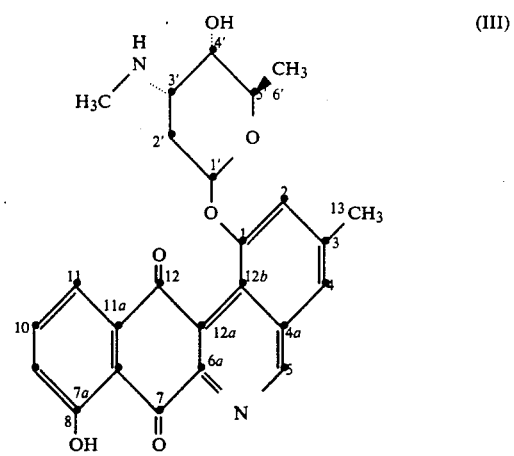

90 MHz-$^{13}$C-NMR (CD$_3$OD): δ=18.3 (qdd, J=127 Hz; C-6'), 22.0 (qt, J=128 Hz; C-13), 29.2 (tm, J=133 Hz; C-2'), 32.5 (qd, J=142 Hz; C-NH), 57.6 (dm, J=148 Hz; C-3'), 69.2 (dm, J=144 Hz; C-4' or C-5'), 69.3 (dm, J=144 Hz; C-4' or C-5'), 99.2 (dm, J=174 Hz; C-1'), 116.1 (tb; C-7a), 119.7 (dd; C-11), 123.4 (C-12b), 124.0 (dddq; C-4), 124.5 (ddq; C-2), 124.9 (dd; C-9), 131.6 (s; C-12a), 133.8 (m; C-11a), 136.6 (d, J=8 Hz; C-4a), 138.4 (d; C-10), 144.9 (q; C-3), 145.4 (d, J=13 Hz; C-6a), 155.0 (sb; C-1), 158.4 (dm, J=184 Hz and J=4 Hz; C-5), 163.1 (dd, J=9 Hz and J=1 Hz; C-8), 186.0 (db, J=4 Hz; C-12), 187.7 (sb; C-7).

The starting culture solution is obtained as follows:
Step 1.1: To prepare the inoculum for the actual production fermentation, a number of yeast/slant agar cultures are inoculated with the strain Streptomyces viridochromogenes (without formation of melanin) DSM 3972, which is kept in ampoules at −80° C., and incubated for 7–10 days at 28° C. These agar cultures have the following composition:

|  | g/l |
| --- | --- |
| yeast extract (Fould Springer) | 4 |
| malt extract (Difco) | 5 |
| glucose | 4 |
| bacto agar | 20 |

The contents of one of these slant agar cultures is subsequently transferred to a 500 ml Erlenmeyer flask with a baffle and containing 100 ml of the medium SCR/9. The medium SCR/9 has the following composition:

|  | g/l |
| --- | --- |
| cerelose (commercial grade glucose) | 22 |
| oxo Lab-Lemco | 5 |
| peptone (Difco) | 5 |
| yeast extract (Difco) | 5 |
| antifoam (Silicone A/AF) | 0.01 |
| casein hydrolysate (Difco) | 3 |
| NaCl | 1.5 |

The Erlenmeyer flask is incubated on a rotary shaker for 48 hours at 28° C. and 250 rpm with a 50 mm throw, after which time the packed mycelial volume of the culture broth (i.e. the cell volume determined by centrifugation for 10 minutes at 1690 g) is 5–8%.

Step 1.2: 25 ml of the culture broth so obtained are then inoculated under aseptic conditions into each of two 2 liter Erlenmeyer flasks with 4 baffles and containing 500 ml of the medium SCR/9. These flasks are incubated for 48 hours at 28° C. and 120 rpm on a rotary shaker with a 50 mm throw, after which time the packed mycelial volume is 10-30%.

Step 1.3: 750 ml (2.5% by volume) of the culture broth obtained in step 1.2 are then transferred under aseptic conditions to a 50 liter preculture fermenter containing 30 liters of the sterile medium SCR/9. The fermenter is equipped with a 6-blade turbine stirrer having a diameter of 115 mm and which rotates at 600 rpm. The incubation conditions are: temperature 28° C.; aeration: 1 liter of air per liter of culture broth per minute; head pressure: 50,000 Pa (0.5 bar); incubation time: 48 hours. The packed mycelial volume is 8-10%.

Step 1.4: 5% by volume of the culture broth obtained in step 1.3 are transferred under aseptic conditions to a fermenter of the same type as used in step 1.3 containing 30 liters of production medium of the following composition:

|  | g/l |
|---|---|
| cerelose (commercial grade glucose) | 20 |
| protaminal (Traders Protein) | 20 |
| yeast extract (Fould Springer) | 10 |
| $KH_2PO_4$ | 0.5 |
| $CaCO_3$ | 3.0 |
| antifoam | as required |

Fermentation is carried out for 7-8 days under the same conditions as in step 1.3. The pH, packed mycelial volume, sterility, temperature, aeration, head pressure and agitation rate are determined at regular intervals. At the end of the fermentation, the pH of the culture broth is >8.0 and the packed mycelial volume is 20-25%.

EXAMPLE 2

278 mg of phenanthroviridine trifluoroacetate are acidified with 50 ml of 0.1N hydrochloric acid (q.v. Example 1) and heated for 30 minutes to 90° C. After cooling the reaction mixture in an ice bath, the dark brown precipitate is isolated by filtration and the filter residue is dissolved in 40 ml of chloroform and the solution is extracted with 10 ml of water. The chloroform phase is dried over sodium sulfate and concentrated under vacuum until the onset of crystallisation. The crystals are filtered with suction and dried under vacuum over phosphorus pentoxide, to give 1,8-dihydroxy-3-methylbenzo[b]phenanthridine-7,12-dione (numbering as in Example 1, formula III); m.p. 234°-235° C.

360 MHz-$^1$H-NMR ($CDCl_3:CD_3OD=9:1$): $\delta=2.6$ (s; 3H, $CH_3$), 7.33 (s; 1H, 9-H), 7.44 (d, J=9 Hz; 1H, 4-H), 7.51 (s; 1H, 11-H), 7.78 (t, J=9 Hz; 1H, 5-H), 7.95 (d, J=9Hz; 1H, 6-H), 9.45 (s; 1H, 12-H).

90 MHz-$^{13}$C-NMR ($CDCl_3:CD_3OD=9:1$): $\delta=20.3$ (C-13), 113.6 (C-7a), 119.5 (C-12b), 120.5 (C-11), 120.7 (C-2), 122.8 (C-4), 124.7 (C-9), 127.5 (C-12a), 131.7 (C-11a), 132.7 (C-4a), 136.3 (C-10), 143.4 (C-3), 144.4 (C-6a), 153.8 (C-1), 159.1 (C-5), 161.0 (C-8), 185.1 (C-12), 188.6 (C-7).

EXAMPLE 3

Pharmaceutical composition for parenteral administration 5 ml of a 1% sterile aqueous solution of phenanthroviridine hydrochloride are filled under aseptic conditions into ampoules or vials and lyophilised. The ampoules or vials are sealed under nitrogen and tested.

EXAMPLE 4

Pharmaceutical composition for parenteral administration 10 ml of a sterile aqueous solution of 0.5% phenanthroviridine hydrochloride and 2.5% of lactose are filled under aseptic conditions into ampoules or vials and lyophilised. The ampoules or vials are sealed and tested.

What is claimed is:

1. A process for the preparation of 1,8-dihydroxy-3-methylbenzo[b]phenanthridine-7,12-dione or its derivative of formula I

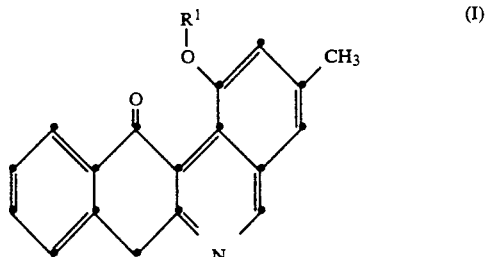

wherein $R^1$ is hydrogen or the radical of formula II

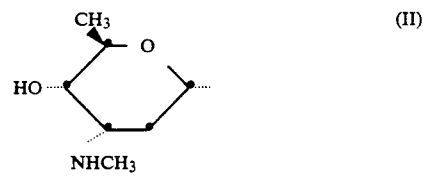

or of a salt of such a compound, wherein $R^1$ is the radical of formula II, which process comprises culturing the strain Streptomyces viridochromogenes (Krainsky) Waksman et Henrici (without formation of melanin) DSM 3972, or a mutant capable of producing the phenanthroidine in a suitable nutrient medium, isolating the compound of formula I, wherein $R^1$ is the radical of formula II, from the culture broth and, if desired, converting the resultant compound into a salt and, if desired, into the compound of formula I, wherein $R^1$ is hydrogen, by treatment with an acid, or an acid ion exchanger.

2. A process according to claim 1, which comprises culturing the strain DSM 3972 or a culture that possesses features of the strain DSM 3972 essential for carrying out said process, under aerobic conditions in an aqueous nutrient medium which contains a carbon source and a nitrogen source as well as inorganic salts, and isolating the compound of formula I, wherein $R^1$ is the radical of formula II and, if desired, converting the resultant compound into a pharmaceutically acceptable salt.

3. A biologically pure culture broth of Streptomyces viridochromogenes Waksman et Henrici (without formation of melanin) DSM 3972 or a biologically pure culture broth containing a mutant capable of producing the phenanthroidine.

4. A biologically pure culture of the strain Streptomyces viridochromogenes Waksman et Henrici (without formation of melanin) DSM 3972.

* * * * *